United States Patent
Chia et al.

[19]

[11] Patent Number: 5,876,399
[45] Date of Patent: Mar. 2, 1999

[54] CATHETER SYSTEM AND METHODS THEREOF

[75] Inventors: Weng-Kwen Raymond Chia, Irvine; Hosheng Tu, Tustin, both of Calif.

[73] Assignee: Irvine Biomedical, Inc., Irvine, Calif.

[21] Appl. No.: 864,716

[22] Filed: May 28, 1997

[51] Int. Cl.[6] .................................................. A61B 17/36
[52] U.S. Cl. ............................ 606/41; 606/45; 607/122; 607/126; 600/374
[58] Field of Search ......................... 606/41, 42, 45–50; 600/374; 607/115, 116, 100–102, 122, 126, 127

[56] References Cited

U.S. PATENT DOCUMENTS

| 4,940,064 | 7/1990 | Desai | 607/122 |
|---|---|---|---|
| 5,238,007 | 8/1993 | Giele et al. | 607/126 |
| 5,324,284 | 6/1994 | Imran | 608/122 |
| 5,492,119 | 2/1996 | Abrams . | |

*Primary Examiner*—Michael Peffley

[57] ABSTRACT

This invention discloses an ablation catheter system with fixation means for use in treatment of cardiac tissues and in other medical applications, such as ablating tumors in a natural body conduit or cavity by applying RF energy, and an inner catheter having alternate energy sources for enhanced ablation. The catheter system passes through a natural body opening to reach the target tissue, where the catheter system stays in a desired position via its fixation means and delivers therapeutic energy selected from the group of laser energy, microwave, inductive radiofrequency and ultrasonic energy to the target tissue for improved treatment.

19 Claims, 3 Drawing Sheets

CATHETER SYSTEM AND METHODS THEREOF

FIELD OF THE INVENTION

The present invention generally relates to novel constructions for a catheter system. More particularly, this invention relates to an ablation catheter system having fixation means and methods for use in conjunction with a catheter comprising an alternate energy source for enhanced treatment of cardiac tissues and in other medical applications, such as ablating tumors in a natural body conduit or cavity.

BACKGROUND OF THE INVENTION

Symptoms of abnormal heart rhythms are generally referred to as cardiac arrhythmias, with an abnormally rapid rhythm being referred to as a tachycardia. The present invention is concerned with the treatment of tachycardias which are frequently caused by the presence of an "arrhythmogenic site" or "accessory atrioventricular pathway" close to the inner surface of the chambers of a heart. The heart includes a number of normal pathways which are responsible for the propagation of electrical signals from upper to lower chamber necessary for performing normal systole and diastole function. The presence of arrhythmogenic site or accessory pathway can bypass or short circuit the normal pathway, potentially resulting in very rapid heart contractions, referred to here as tachycardias.

Treatment of tachycardias may be accomplished by a variety of approaches, including drugs, surgery, implantable pacemakers/defibrillators, and catheter ablation. While drugs may be the treatment of choice for many patients, they only mask the symptoms and do not cure the underlying causes. Implantable devices only correct the arrhythmia after it occurs. Surgical and catheter-based treatments, in contrast, will actually cure the problem, usually by ablating the abnormal arrhythmogenic tissue or accessory pathway responsible for the tachycardia. It is important for a physician to accurately steer the catheter to the exact site for ablation. Once at the site, it is important for a physician to control the emission of energy to ablate the tissue within the heart.

Of particular interest to the present invention are radiofrequency (RF) ablation protocols which have proven to be highly effective in tachycardia treatment while exposing a patient to minimal side effects and risks. Radiofrequency catheter ablation is generally performed after conducting an initial mapping study where the locations of the arrhythmogenic site and/or accessory pathway are determined. After a mapping study, an ablation catheter is usually introduced to the target heart chamber and is manipulated so that the ablation tip electrode lies exactly at the target tissue site. Radiofrequency energy or other suitable energy is then applied through the tip electrode to the cardiac tissue in order to ablate the tissue of arrhythmogenic site or the accessory pathway. By successfully destroying that tissue, the abnormal signal patterns responsible for the tachycardia may be eliminated.

Typically a conventional electrophysiology catheter has had a tip which is very smooth and generally are hemispherically shaped and thus have a tendency to slip around in the chamber of the heart during the pumping of the heart. This is particularly true in certain areas of heart where it is difficult to apply positive pressure to the tip of the catheter. Because of the difficulty of retaining the tip section and the tip of a catheter in certain position, the effectiveness of mapping and ablation is significantly compromised.

The tip section of a catheter is referred to here as the portion of that catheter containing at least one electrode. For illustration purpose, a catheter utilized in the endocardial radiofrequency ablation is inserted into a major vein or artery, usually in the neck or groin area. The catheter is then guided into an appropriate chamber of the heart by appropriate manipulation through the vein or artery. The tip section of a catheter must be manipulatable by a physician from the proximal end of the catheter, so that the electrodes at the tip section can be positioned against the tissue to be ablated. The catheter must have a great deal of flexibility in order to follow the pathway of major blood vessels into the heart. It must permit user manipulation of the tip even when the catheter body is in a curved and/or twisted configuration. The tip section of a conventional electrophysiology catheter that is deflectable usually contains one large electrode about 4 mm in length for ablation purpose. An alternate energy source, in addition to the RF energy, is needed to enhance the ablation effectiveness.

Several patents, such as U.S. Pat. No. 5,500,012 to Brucker et al., U.S. Pat. No. 5,492,119 to Abrams, and U.S. Pat. No. 5,507,802 to Imran, teach the technique for tip fixation means. However, none of them discloses the atraumatic methods of affixing the tip section of a catheter in place.

After the exact location of a target tissue is identified, the ablation catheter may still not easily approach the target site. An external ultrasonic imaging capability therefore becomes in need so that ablation is not taking place in an inappropriate location. The fluoroscope time can be substantially cut short when an external ultrasonic imaging is used instead. In the U.S. Pat. No. 4,794,931, there has been disclosed a catheter and system which can be utilized for ultrasonic imaging. However, there is no disclosure to how such a catheter and system can be utilized in conjunction with an endocardial ablation catheter having a tip section with fixation means to achieve the desired ultrasonic imaging and ultimately the desired ablation.

While an ablation procedure using an existing catheter with radio-frequency energy has had promising results, an alternate energy source can be added to enhance the ablation capability. Such alternate energy sources include laser, microwave, inductive radiofrequency, and ultrasonic energy sources. Therefore there is a need for an improved catheter which can be utilized for mapping and ablation and in which is possible to temporarily affix the tip section of the catheter so that it will remain in a desired position on the wall of the heart during beating of the heart.

SUMMARY OF THE INVENTION

In general, it is an object of the present invention to provide an improved catheter which can be used in mapping and/or ablating cardiac tissue in the wall of a heart and which is provided with appropriate fixation means for retaining the tip section in a desired position on the wall of the heart. The capability of affixing the tip section of the catheter in place may also be applicable to means of ablating the tumors in a body natural conduit or cavity. It is another object of the present invention to provide a catheter with alternate energy sources, such as laser energy, microwave, inductive radiofrequency, and ultrasonic energy for enhanced ablation. It is another object of this invention to provide a catheter system with fixation means and a laser catheter comprising an optical fiber for passing laser energy, an optical fiber port and/or thermocouples on the end of hypodermic tubing.

In one embodiment, a catheter system comprises three major components: a catheter sheath with fixation means comprising a plurality of expandable members on the outside of said catheter system, a catheter assembly in the middle and an inner catheter having alternate energy delivery means at the inner side. In a particular embodiment, the catheter system comprises: a catheter assembly with a tip section, a distal end, a proximal end, and at least one lumen extending therebetween, wherein the tip section comprises at least one electrode; a handle attached to the proximal end of said catheter assembly; an inner catheter, which is located inside the lumen of the catheter assembly, comprising a flexible elongate tubular member having a distal section, a proximal extremity, and a distal extremity, wherein the proximal extremity of the inner catheter is attached to said handle; and a retractable fixation deployment means secured on the outside surface of the catheter assembly.

Said retractable fixation deployment means includes a plurality of spaced apart expandable members, wherein the proximal end of said members is attached to a deployment means at the handle while the distal end of said members is secured at a securing point on the outside surface of the catheter assembly. The catheter system also comprises a non-deployed state for said retractable fixation deployment means when said catheter system is advanced into the body of a patient and/or is removed from the body of a patient, and further comprises a distended deployed state for said retractable fixation deployment means when said catheter system is positioned at the target location of the body.

Another object of the invention is to provide a catheter with retractable fixation deployment means in which the fixation means can be deployed and un-deployed during the mapping and/or ablation operations. Another object of the invention is to provide a catheter with retractable fixation deployment means in which the fixation means can be readily maneuvered, applied, and controlled by a deployment mechanism at the handle. Another object of the invention is to provide a catheter system with the deployment of said expandable members at a pre-determined location along the catheter sheath. Still another object of the invention is to provide a catheter to deliver an alternate energy selected from the group of laser, microwave, inductive radiofrequency, and ultrasonic energy for enhanced ablation.

The catheter system further comprises a steering mechanism at the handle for controlling the deflection of said tip section of the catheter assembly. Usually a rotating ring or a push-pull plunger is employed in the steering mechanism. In another embodiment, the steerable ablation catheter comprises a bidirectional deflection or multiple curves deflection of the tip section having retractable fixation deployment means. One end of the steering wire is attached at certain point of the tip section of the flexible catheter assembly. The other end is attached to the steering mechanism at the handle. The steering mechanism on a steerable catheter or device is well-known to those who are skilled in the art.

At least one conducting wire which is soldered to an electrode, passes through the lumen of the catheter assembly and the interior void of the handle and is thereafter soldered to a contact pin of the connector which is secured at the proximal end of the handle. Therefrom, the conducting wire is connected to an external RF generator for ablation operations and/or to an EKG monitor for recording and displaying of the endocardial electrical signal.

In an additional embodiment, the catheter system further comprises a temperature sensing and close-loop temperature control mechanism for the catheter system having at least one temperature sensor on the distal section of the catheter assembly or on the inner catheter. The location of the temperature sensor is preferably in the very proximity of one of the electrodes. In a still further embodiment, a method for operating an ablation catheter system of this invention further comprises a programmed temperature control mechanism for independently controlling the delivery of RF energy of each electrode of the ablation catheter.

In a still further embodiment, the distal section of the catheter assembly comprises at least one electrode, which is formed of a conducting material, wherein the material for the electrode may consist of conductive metals selected from the group of platinum, iridium, gold, silver, stainless steel, Nitinol, or an alloy of their mixture. The conducting metal and its fabrication to form an electrode to be used in a catheter is well known to those who are skilled in the art.

The catheter system of this invention further comprises a plurality in excess of two spaced apart expandable members for the retractable fixation deployment means. In a preferred embodiment, the catheter system comprises a plurality in excess of four spaced apart expandable members for the retractable fixation deployment means. The construction material for the expandable members may be selected from the group of polyethylene, polyurethane, polyether block amide polymer, stainless steel, high strength Nitinol and the like. The expandable members are secured on the exterior surface of the catheter assembly which has a continuous linear smooth surface when the retractable fixation deployment means is at its un-deployed state. The expandable members have a preshaped memory and may extend to their preformed shape when the retractable fixation deployment means is deployed. The location of the deployed expandable members on the catheter sheath can be pre-determined.

In another embodiment, the catheter system of this invention further comprises expandable members of said retractable fixation deployment means having a preshaped memory, and extending at an angle of less than 90 degrees, preferably less than 45 degrees, relative to the proximal side of the longitudinal axis of the catheter assembly when the deployment means is deployed. In a further embodiment, the catheter system further comprises expandable members of said retractable fixation deployment means having a preshaped memory, and extending with a curved concave or convex fashion at an acute angle relative to the proximal side of the longitudinal axis of the catheter assembly when the deployment means is deployed.

In one embodiment, the inner catheter is an ablation catheter which delivers alternate energy, such as laser, microwave, inductive radiofrequency, and ultrasonic energy for enhanced ablation to the myocardium to destroy selected myocardial tissue.

A method for operating a catheter system comprises: introducing the catheter system having an inner catheter, a middle catheter assembly and an outer catheter sheath with retractable fixation deployment means under a non-deployed state, into the body through a natural body opening; and once approaching the target tissue, deploying the retractable fixation deployment means of said catheter sheath by a deployment mechanism located at the handle. The method for operating a catheter system of this invention further comprises at least one electrode mounted on the tip section of the flexible elongate tubular member of the catheter assembly. The method for operating a catheter system further comprises measuring the endocardial electricity from or applying RF energy to the at least one electrode on the distal section of the catheter assembly. The method for operating a catheter system further comprises applying the alternate energy source through the inner catheter for enhanced ablation.

Another object of the invention is to provide a catheter and methods in which it is possible to view the area to be ablated prior to ablation to ensure that ablation is being carried out in an appropriate location. The tip section of the catheter assembly having a catheter sheath with retractable fixation deployment means is encoded with at least one marker which is visible to ultrasonic energy. The marker has been provided in the form of encapsulated air bubble.

A fluid conveying lumen is preferably disposed within the catheter assembly along the longitudinal axis thereof The lumen is adapted to communicate with a fluid supply source to convey fluid from the source and through the lumen to be discharged through the opening of the distal end of the catheter system. The fluid conveyed in this invention may include the cooled saline, the antibiotics, the heparin, the chemotherapy fluids or other therapeutic fluids.

In one embodiment, the invention also comprises a method and system for controlling the flow rate of fluid through the lumen to optimize the cooling effect of the energy delivering inner catheter. The control system preferably regulates the flow rate based on signals representative of the temperature of the catheter tip and/or tissue impedance.

The catheter system of the present invention has several significant advantages over known catheters or ablation techniques. In particular, the catheter system having a retractable fixation deployment means and an inner catheter with alternate energy sources may result in firm and intimate tissue contact between the tip and the target tissue during tissue ablation, resulting in deep and large lesions which are highly desirable in tachycardiac treatment.

BRIEF DESCRIPTION OF THE DRAWINGS

Additional objects and features of the present invention will become more apparent and the invention itself will be best understood from the following Detailed Description of the Preferred Embodiments, when read with reference to the accompanying drawings.

DETAILED DESCRIPTION OF THE PREFERRED EMBODIMENTS

Figure 1:
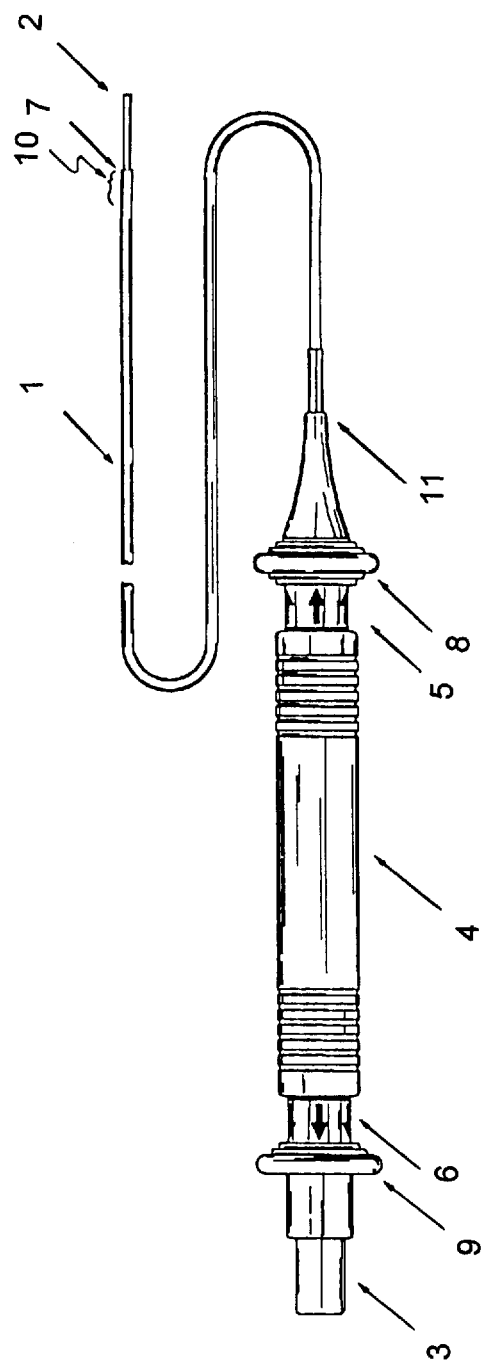
FIG. 1 is an overall view of the catheter system having a retractable fixation deployment means and an inner catheter constructed in accordance with the principles of the present invention.

FIG. 1 shows an overall view of the catheter system having a retractable fixation deployment means. A catheter system constructed in accordance with the principles of the present invention comprises: a catheter assembly 1 having a distal tip section 10, a distal end 7, a proximal end 11, and at least one lumen extending therebetween. The catheter also comprises an inner catheter 2 which may extend out of the catheter assembly 1 and is located within the lumen of the catheter assembly 1. A handle 4 is attached to the proximal end 11 of said catheter assembly 1.

A connector 3 secured at the proximal end of the catheter system, is part of the handle 4. The handle has one steering mechanism 5. The steering mechanism 5 is to deflect the tip section 10 of the catheter assembly for catheter maneuvering and positioning. By pushing forward the front plunger 8 of the steering mechanism 5 on the handle 4, the tip section 10 of the catheter assembly 1 deflects to one direction. By pulling back the front plunger 8, said tip section returns to its neutral position. In another embodiment, the steering mechanism 5 at the handle 4 comprises means for providing a plurality of deflectable curves on the distal tip section 10 of the catheter assembly 1.

Figure 2:
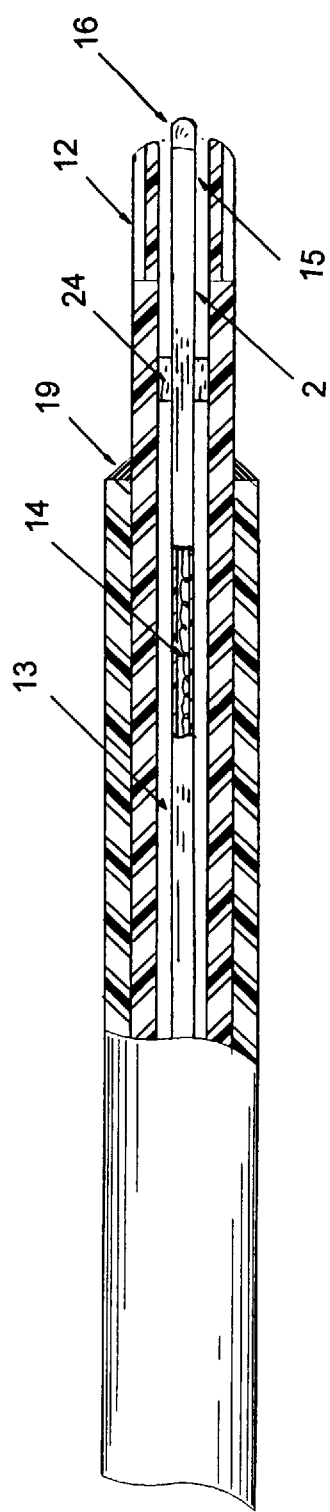
FIG. 2 is a close-up view of the distal section of the catheter system at non-deployed state.

FIG. 2 shows a close-up view of the distal section of the catheter system having retractable fixation deployment means at non-deployed state. In one embodiment, the tip section 10 of the catheter assembly 1 has at least one electrode 12. The electrode is constructed of a conducting material. The center lumen 13 of the catheter assembly has an inner catheter 2, comprising a tip section 15. In one embodiment, at least one electrode 16 is located at the tip section 15. In another embodiment, the inner catheter 2 is an ablation catheter which delivers an alternate energy such as laser, microwave, inductive radiofrequency and/or ultrasonic energy to the target tissue. In a further alternate embodiment, at least an electrode 16 is located at the distal section of the inner catheter 2.

Figure 3:
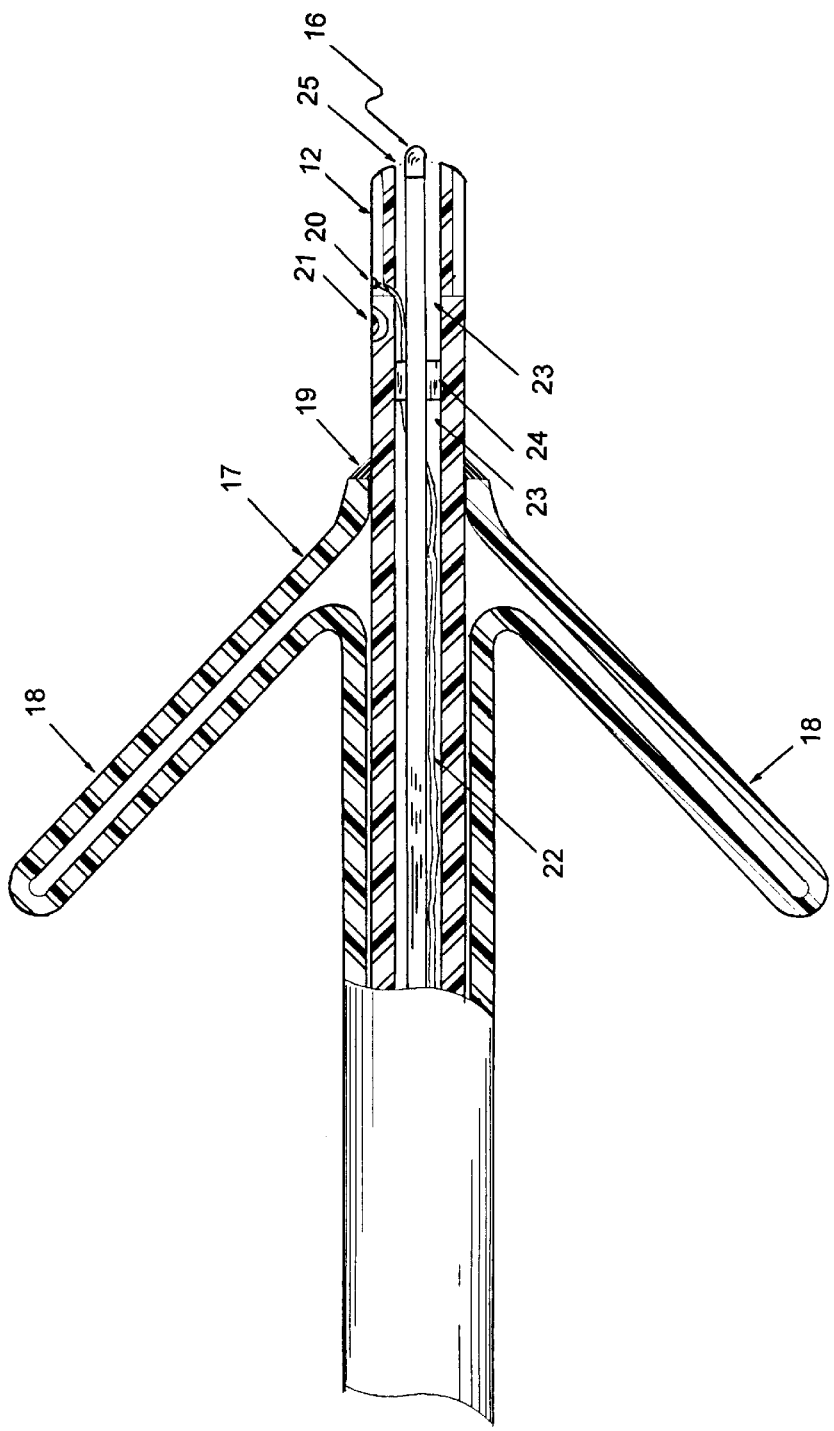
FIG. 3 is a close-up view of the distal section of the catheter system at fully deployed state.

FIG. 3 shows a close-up view of the distal section of the catheter system having retractable fixation deployment means 17 at deployed state. The deployment of the retractable fixation deployment means 17 is controlled by a deployment mechanism 6 at the handle 4 (FIG. 1). A controlling ring 9 is used to deploy the retractable fixation deployment means 17 secured at the outside surface of the catheter assembly 1. A plurality of the expandable members 18 of the retractable fixation deployment means 17 has a preshaped memory. The expandable members 18 extend with a curved concave or convex fashion at an acute angle relative to the proximal side of the longitudinal axis of the catheter assembly 1 when the deployment means 17 is deployed. The retractable fixation deployment means 17 is secured at a securing point 19 on the surface of the catheter assembly 1, wherein the securing point is located proximal to the tip section 10 of the catheter assembly The catheter system has at least one temperature sensor 20 and ultrasonic imaging capabilities. In order to enhance the ablation positioning of said ablation catheter, the electrode is encoded with at least one marker 21 which is visible to ultrasonic energy. Such marker 21 is provided in the form of encapsulated air bubbles. The marker 21 is placed in the proximity of the electrodes 12 or 16 in a way so that the exact location of the distal section 10 is visible to an external ultrasonic energy. By way of example, the bubble in a marker can be formed by introducing air by a syringe (not shown) penetrating the wall of the substrate assembly of said catheter assembly and thereafter is sealed by epoxy.

The electrode has an insulated conducting wire (not shown) secured to the electrode, which passes through the lumen 13 of the catheter assembly 1 and is soldered to a contact pin of the connector 3 at the proximal end of the handle 4. The conducting wire from the connector end is externally connected to an EKG for diagnosis or to an RF generator during an electrophysiology ablation procedure. Therefrom, the RF energy is transmitted through the conducting wire to the electrode and delivered the energy to the target tissue.

A temperature sensor 20, either a thermocouple means or a thermister means, is constructed at the proximity of the electrode 12 or 16 to measure the tissue contact temperature when an RF energy and/or an alternate energy is delivered.

The temperature sensing wire 22 from the thermocouple or thermister is connected to one of the contact pins (not shown) of the connector 3 and externally connected to a transducer and to a temperature controller. The temperature reading is thereafter relayed to a close-loop control mechanism to adjust the RF energy output. The RF energy delivered is thus controlled by the temperature sensor reading or by a pre-programmed control algorithm.

To prevent blood from backflow into the proximal end of the lumen of the fluid conveying duct 23, a silicone type check valve 24 is installed at certain opening of the lumen of the fluid conveying duct 23. The fluid conveying duct 23 is extended all the way to the distal end of the catheter assembly and has an opening 25 at the distal end of said catheter system.

In another embodiment, the catheter of this invention provides fluid communication and commensurate flow of fluid originating inside the tip section 10 of the catheter assembly 1 to the distal exterior surface of the catheter system through a front opening 25, which directs the fluid flow from inside the lumen 14 of the inner catheter 2 over the exterior surface of the catheter to provide a fluid protective layer surrounding the energy delivering catheter to minimize temperature elevation of the electrode with biological tissues.

From the foregoing, it should now be appreciated that an improved ablation catheter having retractable fixation deployment means has been disclosed for mapping and/or ablation procedures, including endocardial, epicardial, or body tissue. While the invention has been described with reference to a specific embodiment, the description is illustrative of the invention and is not to be construed as limiting the invention. Various modifications and applications may occur to those skilled in the art without departing from the true spirit and scope of the invention as described by the appended claims.

What is claimed is:

1. A catheter system comprising:
   (a) a catheter assembly with a tip section, a distal end, a proximal end, a surface, and at least one lumen extending therebetween, wherein the tip section has at least one electrode;
   (b) a handle attached to the proximal end of said catheter assembly;
   (c) a catheter sheath having a retractable fixation deployment means secured at a securing point on the surface of the catheter assembly, wherein the securing point is located proximal to the tip section of the catheter assembly, and wherein said retractable fixation deployment means includes a plurality of spaced apart expandable members, comprising a non-deployed state for said retractable fixation means when said catheter system is advanced into the body of a patient and/or removed from the body, and further comprising a distended deployed state for said retractable fixation deployment means when said catheter system is inside the body of a patient;
   (d) an inner catheter, which is located inside the at least one lumen of the catheter assembly, comprising a flexible elongate tubular member having a distal section, and proximal and distal extremities, wherein said proximal extremity of the inner catheter is attached to the handle.

2. The catheter system of claim 1, wherein the inner catheter is an ablation catheter which is connected to deliver alternate energy for enhanced ablation.

3. The catheter system of claim 2, wherein the alternate energy is selected from the group of laser energy, microwave, inductive radiofrequency and ultrasonic energy.

4. The catheter system as in claim 3 further comprising means for supplying a fluid the distal section of the inner catheter.

5. The catheter system of claim 4, wherein the fluid conveyed is selected from the group of saline, antibiotics, heparin, chemotherapy fluids, and therapeutic fluids.

6. The catheter system as in claim 3 further comprising at least one electrode mounted on the distal section of the inner catheter.

7. The catheter system as in claim 6 further comprising ultrasonic visible markers being disposed on the tip section of the catheter assembly.

8. The catheter system as in claim 3 further comprising a steering mechanism at the handle for controlling the deflection of the tip section of the catheter assembly.

9. The catheter system of claim 8, wherein said steering mechanism provides a plurality of deflectable curves on the tip section of the catheter assembly.

10. The catheter system of claim 8, wherein said expandable members of said retractable fixation deployment means have a preshaped memory, and extend at an angle of less than 90 degrees relative to the longitudinal axis of the catheter assembly when the deployment means is deployed.

11. The catheter system of claim 8, wherein said expandable members of said retractable fixation deployment means have a preshaped memory, and extend with a curved fashion at an acute angle relative to the longitudinal axis of the catheter assembly when the deployment means is deployed.

12. The catheter system as in claim 8 further comprising a temperature sensor at the tip section of the catheter assembly and a close-loop temperature control mechanism for the catheter system.

13. A method for operating a catheter system, the catheter assembly having a tip section, a distal end, a proximal end, a surface, and at least one lumen extending therebetween, wherein the tip section has at least one electrode; a handle attached to the proximal end of said catheter assembly; a catheter sheath having a retractable fixation deployment means secured at a securing point on the surface of the catheter assembly, wherein the securing point is located proximal to the tip section of the catheter assembly, and wherein said retractable fixation deployment means includes a plurality of spaced apart expandable members, comprising a non-deployed state for said retractable fixation means when said catheter system is advanced into the body of a patient and/or removed from the body, and further comprising a distended deployed state for said retractable fixation deployment means when said catheter system is inside the body of a patient; an inner catheter, which is located inside the lumen of the catheter assembly, comprising a flexible elongate tubular member having a distal section, and proximal and distal extremities, wherein said proximal extremity of the inner catheter is attached to the handle, and wherein at least one electrode is mounted on the tip section of the inner catheter;

the method comprising:
   introducing the catheter system having an inner catheter, a catheter assembly and an outer catheter sheath with a retractable fixation deployment means under a non-deployed state, into the body through a natural body opening;
   once approaching the target tissue, deploying the retractable fixation deployment means of said catheter sheath by a deployment mechanism located at the handle;

measuring the endocardial electricity from or applying alternate energy to the at least one electrode on the distal section of the inner catheter; and applying the alternate energy source for enhanced ablation.

14. The method for operating a catheter system of claim 13, wherein the alternate energy is selected from the group of laser energy, microwave, inductive radiofrequency and ultrasonic energy.

15. The method for operating a catheter system as in claim 13 further comprising moving the electrode into position by using at least one ultrasonically visible marker.

16. The method for operating a catheter system as in claim 13, further comprising a steering mechanism at the handle for controlling the deflection of the tip section of the catheter assembly.

17. The method for operating a catheter system of claim 14, wherein said expandable members of said retractable fixation deployment means have a preshaped memory, and extend with a curved fashion at an acute angle relative to the longitudinal axis of the catheter assembly when the deployment means is deployed.

18. A tissue ablation catheter system comprising:

a catheter assembly with a distal section, a distal end, a proximal end, an exterior surface, and at least one lumen extending therebetween;

a handle attached to the proximal end of said catheter assembly;

a catheter sheath having a retractable fixation deployment means secured at a securing point on the exterior surface of the catheter assembly, wherein the securing point is located proximal to the tip section of the catheter assembly, and wherein said retractable fixation deployment means including a plurality of spaced apart expandable members, comprising a non-deployed state for said retractable fixation means when said catheter system being advanced into the body of a patient and/or being removed from the body, and further comprising a distended deployed state for said retractable fixation deployment means when said catheter system is positioned inside the body of a patient; and an inner catheter, which is located inside the at least one lumen of the catheter assembly, comprising a flexible elongate tubular member having a distal section, and proximal and distal extremities, wherein said proximal extremity of the inner catheter is attached to the handle.

19. The tissue ablation catheter system of claim 18, wherein said inner catheter is an ablation catheter which is adapted to deliver alternate energy selected from the group of laser energy, microwave, inductive radiofrequency and ultrasonic energy.

* * * * *